(12) United States Patent
De Pater et al.

(10) Patent No.: US 9,056,897 B2
(45) Date of Patent: Jun. 16, 2015

(54) METHOD FOR ISOLATING A CYCLOHEXAPEPTIDE

(75) Inventors: Robertus Mattheus De Pater, Echt (NL); Dhiredj Chandre Jagesar, Echt (NL)

(73) Assignee: DSM SINOCHEM PHARMACEUTICALS, Delft (NL)

( * ) Notice: Subject to any disclaimer, the term of this patent is extended or adjusted under 35 U.S.C. 154(b) by 97 days.

(21) Appl. No.: 13/876,227

(22) PCT Filed: Sep. 26, 2011

(86) PCT No.: PCT/EP2011/066650
§ 371 (c)(1),
(2), (4) Date: Mar. 27, 2013

(87) PCT Pub. No.: WO2012/041801
PCT Pub. Date: Apr. 5, 2012

(65) Prior Publication Data
US 2013/0184433 A1    Jul. 18, 2013

(30) Foreign Application Priority Data
Sep. 28, 2010  (EP) .................................... 10180641

(51) Int. Cl.
| *A61K 38/12* | (2006.01) |
| *A61K 38/08* | (2006.01) |
| *C07K 7/64* | (2006.01) |
| *C07K 1/36* | (2006.01) |
| *C07K 1/20* | (2006.01) |
| *C07K 1/18* | (2006.01) |
| *C07K 1/16* | (2006.01) |
| *C07K 1/14* | (2006.01) |
| *C07K 7/56* | (2006.01) |

(52) U.S. Cl.
CPC ... *C07K 1/36* (2013.01); *C07K 7/56* (2013.01); *C07K 7/64* (2013.01)

(58) Field of Classification Search
CPC ....... A61K 38/12; A61K 38/08; A61K 38/04; C07K 1/36; C07K 1/20; C07K 1/18; C07K 1/16; C07K 1/14; C07K 7/64; C07K 7/56; C07K 7/00; G01N 23/2055; G01N 23/00
See application file for complete search history.

(56) References Cited

U.S. PATENT DOCUMENTS

| 4,310,518 A | 1/1982 | Freidinger et al. | |
| 2009/0324635 A1* | 12/2009 | Korodi et al. | 424/195.15 |
| 2010/0256074 A1* | 10/2010 | Eidelman et al. | 514/21.1 |

FOREIGN PATENT DOCUMENTS

| WO | WO 2005/026323 | 3/2005 |
| WO | WO 2009/142761 | 11/2009 |
| WO | WO 2009/158034 | 12/2009 |
| WO | WO 2010/008493 | 1/2010 |
| WO | WO 2010/108637 | 9/2010 |

* cited by examiner

*Primary Examiner* — Karlheinz R Skowronek
*Assistant Examiner* — Catherine Mader
(74) *Attorney, Agent, or Firm* — Nixon & Vanderhye P.C.

(57) ABSTRACT

The present invention relates to a method for isolating acyclohexapeptide and to a novel crystalline form of caspofungin diacetate thus obtained.

11 Claims, 1 Drawing Sheet

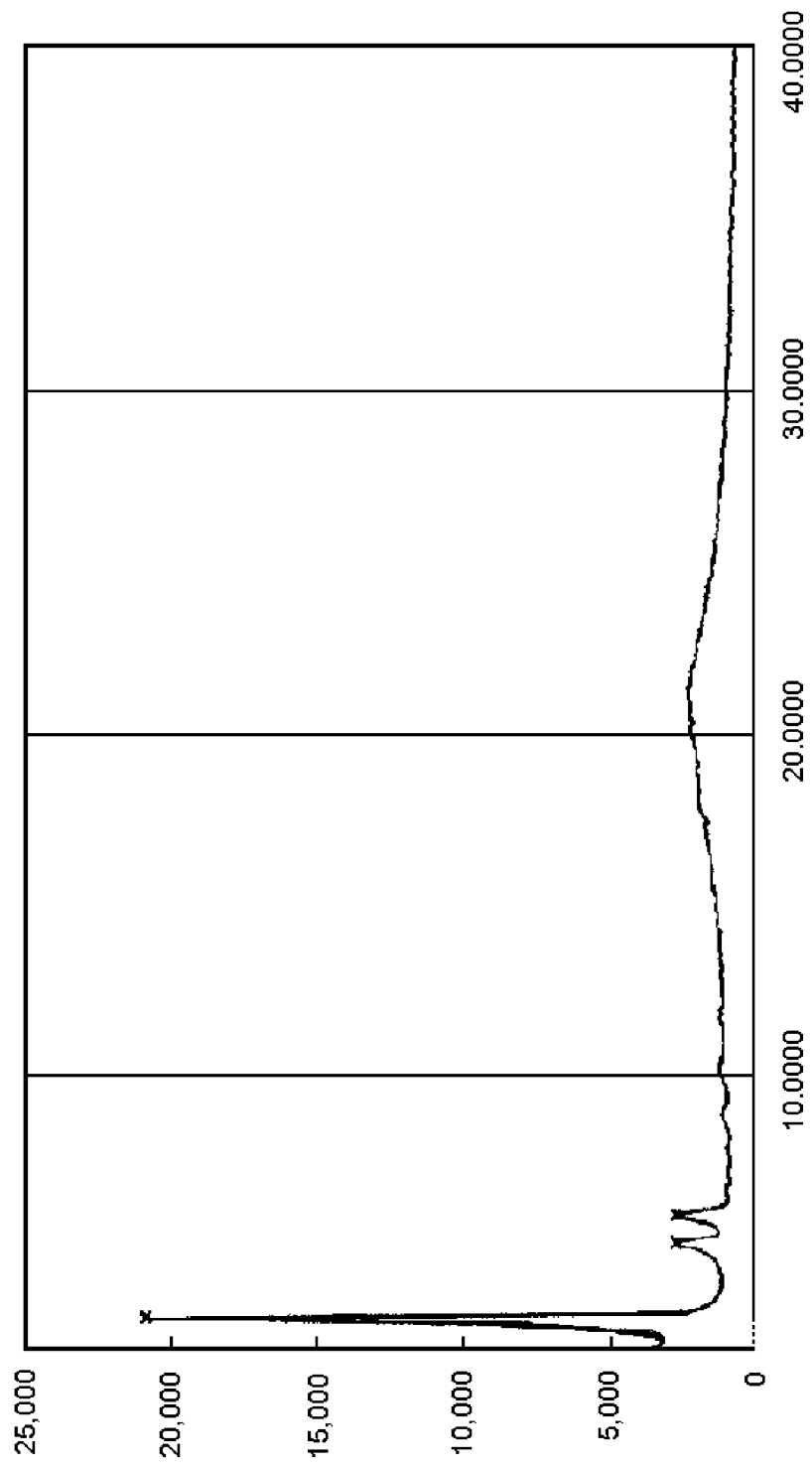

METHOD FOR ISOLATING A CYCLOHEXAPEPTIDE

This application is the U.S. national phase of International Application No. PCT/EP2011/066650 filed 26 Sep. 2011 which designated the U.S. and claims priority to EP 10180641.2 filed 28 Sep. 2010, the entire contents of each of which are hereby incorporated by reference.

FIELD OF THE INVENTION

The present invention relates to a method for isolating a cyclohexapeptide and to a novel crystalline form of caspofungin diacetate thus obtained.

BACKGROUND OF THE INVENTION

Cyclopeptides are polypeptides in which the terminal amine and carboxyl groups form an internal peptide bond. Several cyclopeptides are known for their advantageous medicinal properties. An excellent example of this is the class of echinocandins which are potent antifungals. Cyclopeptides can be naturally occurring compounds but may also be obtained by total synthesis or by synthetic or genetic modification of naturally occurring or naturally produced precursors; the latter class is referred to as semi synthetic cyclopeptides. Examples of medicinally useful echinocandins are the cyclohexapeptides anidulafungin, caspofungin, cilofungin and micafungin which are useful in treating fungal infections especially those caused by *Aspergillus, Blastomyces, Candida, Coccidioides* and *Histoplasma*. Anidulafungin (1-[(4R,5R)-4,5-dihydroxy-$N^2$-[[4"-(pentyloxy)[1,1':4',1"-terphenyl]-4-yl]carbonyl]-L-ornithine]echinocandin B; (1a) with $R_1$=—OH, $R_2$=—C(O)-$pC_6H_4$-$pC_6H_4$-$pC_6H_4$—O($CH_2$)$_4$ $CH_3$, $R_3$=—H, $R_4$=—$CH_3$, $R_5$=—$CH_3$), caspofungin (1-[(4R,5S)-5-[(2-aminoethyl)amino]-$N^2$-(10,12-dimethyl-1-oxotetradecyl)-4-hydroxy-L-ornithine]-5-[(3R)-3-hydroxy-L-ornithine]-pneumocandin $B_0$; (1b) with $R_1$=—NH($CH_2$)$_2$ $NH_2$, $R_2$=—C(O)($CH_2$)$_8$CH($CH_3$)$CH_2$CH($CH_3$)$CH_2$CH$_3$, $R_3$=—H, $R_4$=—($CH_2$)$_2$NH$_2$, $R_5$=—H) and micafungin (1-

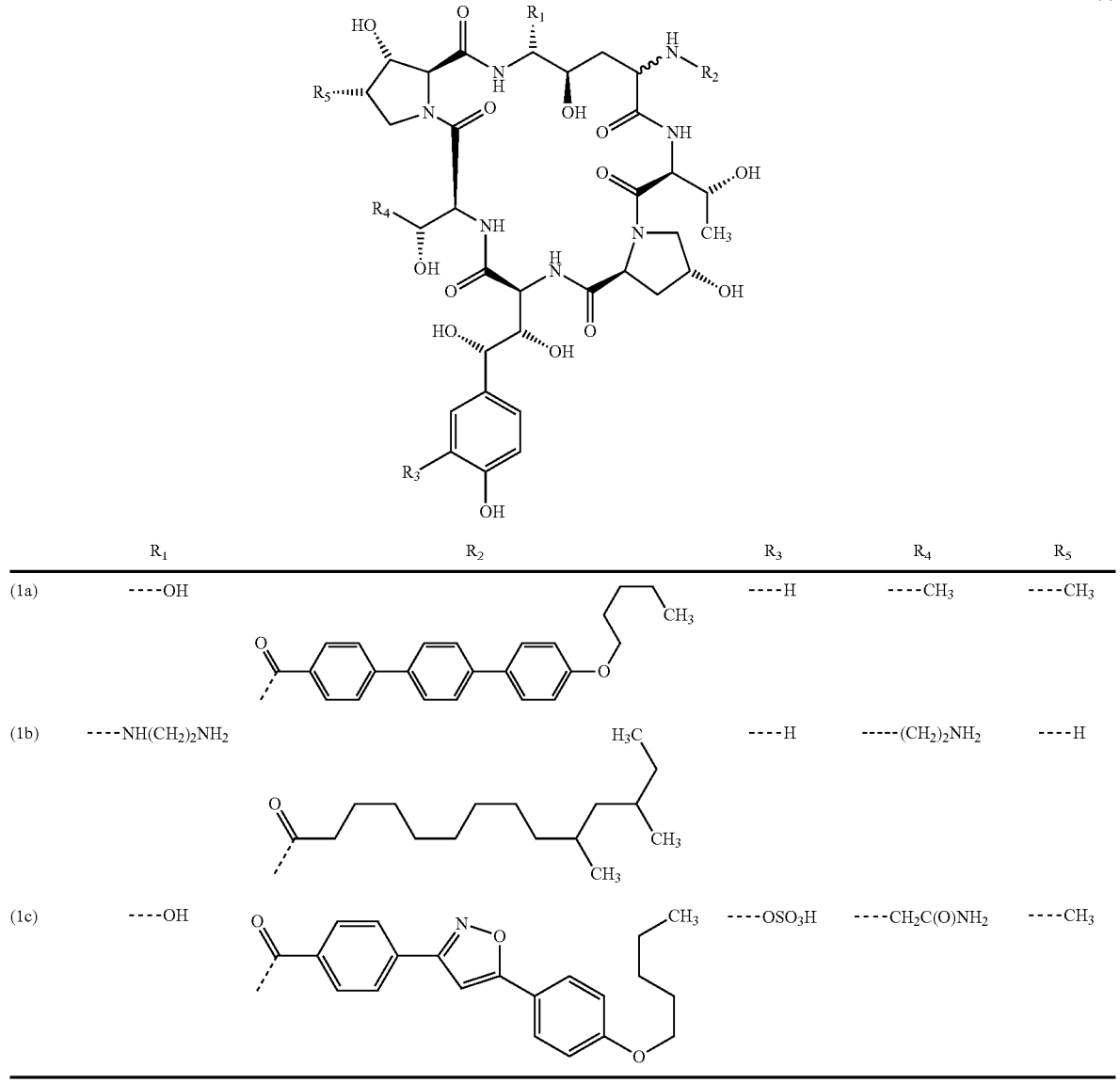

[(4R,5R)-4,5-dihydroxy-$N^2$-[4-[5-[4-(pentyloxy)phenyl]-3-isoxazolyl]benzoyl]-L-ornithine]-4-[(4S)-4-hydroxy-4-[4-hydroxy-3-(sulfooxy)phenyl]-L-threonine]pneumocandin $A_0$; (1c) with $R_1$=—OH, $R_2$=-[4-[5-[4-(pentyloxy)phenyl]-3-isoxazolyl]benzoyl]-L-ornithine], $R_3$=—$OSO_3H$, $R_4$=—$CH_2C(O)NH_2$, $R_5$=—$CH_3$) are all semi synthetic cyclohexapeptides derivable from naturally occurring echinocandins such as for instance echinocandin B, pneumocandin $A_0$ or pneumocandin $B_0$.

Although nature can provide a substantive part of the complex chemical structure of semi synthetic cyclohexapeptides, and in many cases having all chiral centers in the required configuration, a major disadvantage nevertheless is that during fermentation often side products are formed that carry through the process and eventually end up as impurities. Only in few cases can fermentation processes be tuned in such a way as to prevent formation of impurities. Particularly when these impurities are structurally closely related to the main product, their removal is usually tedious and often requires unprecedented purification approaches as the main products in question are chemically unstable and/or prone to racemization.

For example, the preparation of caspofungin (1b) from fermentatively obtained pneumocandin $B_0$ (1 with $R_1$=—OH, $R_2$=—$C(O)(CH_2)_8CH(CH_3)CH_2CH(CH_3)CH_2CH_3$, $R_3$=—H, $R_4$=—$CH_2C(O)NH_2$ and $R_5$=—H) is a process wherein removal of impurities is an important issue. A multitude of structurally related impurities occurring during fermentation of pneumocandin $B_0$ has been described. Examples are compounds having an additional methyl function (such as pneumocandin $A_0$, pneumocandin $A_1$, pneumocandin $A_2$, pneumocandin $A_3$, pneumocandin $A_4$, pneumocandin $A_5$, pneumocandin $A_6$), compounds lacking one or two hydroxyl groups (such as pneumocandin $B_1$, pneumocandin $B_2$, pneumocandin $B_5$, pneumocandin $B_6$, pneumocandin $E_0$), compounds having a 4-hydroxy proline rather than a 3-hydroxy proline moiety (pneumocandin $C_0$), compounds having additional hydroxyl groups (such as pneumocandin $D_0$, pneumocandin $D_2$) or the recently described impurity A (US 2009/0324635) wherein, in the caspofungin structure, one of the hydroxy-L-ornithine moieties is replaced by an L-serine moiety.

Recently, in WO 2010/008493 a process was disclosed for preparing azacyclohexapeptide salts comprising spray drying or precipitating by addition of an anhydrous organic solvent. Although the method leads to caspofungin of high purity, precipitation also has the disadvantage of being a method known for forming solid particles that can easily include unwanted impurities.

In view of the strict regulatory and health-related requirements there remains a need for ever-improved purification and isolation methods.

DETAILED DESCRIPTION OF THE INVENTION

In a first aspect, disclosed is a method for isolating a cyclohexapeptide comprising the subsequent steps of:
(a) Contacting a solution comprising a cyclohexapeptide and water with a resin;
(b) Removing the liquid phase from the mixture obtained in step (a);
(c) Eluting said cyclohexapeptide by contacting the material retained after removal of the liquid phase in step (b) by addition of an organic solvent;
(d) Separating resin from the mixture obtained in step (c);
(e) Crystallizing said cyclohexapeptide from the solution retained after removal of said resin
(f) Isolating said cyclohexapeptide from the mixture obtained in step (e)

Following isolation the cyclohexapeptide obtained after step (f) may be dried in order to obtain a product with a reduced content of water. The advantage of an additional drying procedure is that the resulting product is more easily handled, is less prone to the formation of unwanted impurities and is consequently of higher purity. Said drying may be carried out by procedures known to the skilled person such as heating, applying reduced pressure, passing a stream of a gas over the isolated product or combinations thereof. Heating may be from temperatures ranging from 15° C. to 80° C. or from 20° C. to 60° C. or from 30° C. to 40° C. Suitable gases are air or inert gasses such as nitrogen or noble gases such as argon, helium, neon or xenon.

Notably said cyclohexapeptide is a compound of general formula (1). $R_1$ may be —$OR_6$ or —$NH(CH_2)_2NHR_7$ with $R_6$ is —H or an acyl, alkyl, aryl, thioalkyl or thioaryl group such as 4-methoxythiophenyl and thiophenyl and $R_7$ is —H or an acyl, alkyl or aryl group. $R_2$ may be —H or $C(O)R_8$ with $R_8$ is —H or a group comprising from 10 to 25 carbon atoms such as -p$C_6H_4$-p$C_6H_4$-p$C_6H_4$—$O(CH_2)_4CH_3$, —$(CH_2)_8CH(CH_3)CH_2CH(CH_3)CH_2CH_3$ or -[4-[5-[4-(pentyloxy)phenyl]-3-isoxazolyl]benzoyl]-L-ornithine]. $R_3$ may be —OH or —H. $R_4$ may be —$CH_3$ or —$(CH_2)_2NHR_7$ or —$CH_2C(O)NHR_7$ with $R_7$ as described above. $R_5$ may be —$CH_3$ or —H. Preferably said cyclohexapeptide is anidulafungin (1a; $R_1$=—OH, $R_2$=—$C(O)$-p$C_6H_4$-p$C_6H_4$-p$C_6H_4$—$O(CH_2)_4CH_3$, $R_3$=—H, $R_4$=—$CH_3$, $R_5$=—$CH_3$), caspofungin (1b; $R_1$=—$NH(CH_2)_2NH_2$, $R_2$=—$C(O)(CH_2)_8CH(CH_3)CH_2CH(CH_3)CH_2CH_3$, $R_3$=—H, $R_4$=—$(CH_2)_2NH_2$, $R_5$=—H), micafungin (1c; $R_1$=—OH, $R_2$=[4-[5-[4-(pentyloxy)phenyl]-3-isoxazolyl]benzoyl]-L-ornithine], $R_3$=—$OSO_3H$, $R_4$=—$CH_2C(O)NH_2$, $R_5$=—$CH_3$) or the like. The cyclohexapeptides described above may be prepared following procedures known to the skilled person such as total chemical synthesis or semi-synthesis, i.e. fermentation followed by one or more chemical conversions. One example may be the conversion of pneumocandin $B_0$ into caspofungin through phenylthio pneumocandin $B_0$ amine as described in U.S. Pat. No. 5,552,521 or U.S. Pat. No. 5,936,062.

The resin may be any chromatographic material such as hydrophobic interaction chromatography material, reversed phase chromatography material, ion-exchange chromatography material or a mixture of two or more of these materials. Examples of resins suitable for the purpose of the present invention are Amberchrom XT 30, Amberchrom CG 300S, Amberchrom CG 300sd, Amberchrom CG 300XT, Amberchrom CG-71, Amberchrom CG-161, Toyopearl's Butyl-650, Ether-650, Hexyl-650, Phenyl-650 and the like. The cyclohexapeptide may be contacted with the resin in various ways. This may be achieved by combining a solution, such as an aqueous solution, of the cyclohexapeptide with the resin in a vessel. The resulting mixture may be stirred to improve adsorption. Removal of resin and/or liquid in the subsequent may be performed by centrifugation, filtration or sedimentation or similar techniques. Alternatively the resin may be packed into a column and the solution of the cyclohexapeptide may be brought onto the column.

The resin may be washed after the solution of the cyclohexapeptide has been contacted with the resin in step (a). Such a washing step will remove impurities that do not adsorb to the resin. The washing may be carried out with various solvents; for most cyclohexapeptides water or a mixture of water with a water-miscible solvent is preferred. Water-miscible solvent in this respect refers to a solvent in which the solubility of water is at least 5% (w/w). Examples are alcohols, ketones, acetonitrile and the like. Specifically short-chain alcohols may be used, examples of which are ethanol, isopropanol, n-propanol and methanol. The washing step should be performed before elution step (c) and may be performed before or after removal of the liquid in step (b).

The solution used in step (a) may also contain a water-miscible solvent.

The organic solvent used for elution in step (c) may be a water-miscible organic solvent. The solvent may be mixed with water such as for example mixtures of ethanol/water wherein the amount of water is from 1-20% (w/w) or from 5-15% (w/w). The solvents used in steps (a) and (c) may be the same but can also be different. The latter is a great advantage as it gives high flexibility when a switch from one solvent to the other is required. A first solvent may be preferable for synthetic purposes whereas another, second, solvent may be preferable for crystallization purposes.

One advantage of the method of the invention is that the concentration of the cyclohexapeptide in solution before applying the method, i.e. as in step (a), may be increased during the process. Consequently the concentration of said cyclohexapeptide in the solution of step (a) may be from 2 to 50 times lower than the concentration of said cyclohexapeptide in the solution retained after removal of said resin in step (d). Usually an increase in concentration is advantageous for the subsequent crystallization and isolation steps (e) and (f) as loss of product in the mother liquor is reduced. For example, the concentration of said cyclohexapeptide in step (a) may be from 0.1 to 5 g·l$^{-1}$ where the concentration of said cyclohexapeptide in the solution retained after removal of the resin in step (d) may be from 5 to 40 g·l$^{-1}$. The latter concentration range still is relatively low as crystallization of cyclohexapeptides from solutions having concentrations ranging from 5 to 40 g·l$^{-1}$ has not been reported yet.

Another advantage of the method of the present invention is that isolation, such as crystallization, may be carried out following step (d) without intermediate concentration step, a methodology described in prior art documents. Clearly the present approach avoids this additional process step which leads to a decrease in yield loss and lesser impurities.

Another advantage is that the liquid wherein the cyclohexapeptide is dissolved may be replaced or partially replaced with another liquid during the method of the present invention. This may be advantageous for controlling yield and purity of the final crystalline product. For example, the amount of water in the solution of step (a) may be from 75% to 95% whereas the amount of water in the solution retained after removal of the resin in step (d) may be less than 10%, for example 5% or even less than 0.5%. Consequently the present invention advantageously provides a method through which highly diluted cyclohexapeptides can be isolated in good to high yields. The method is simple, does not require expensive and/or complex equipment and does not require energy-consuming evaporation techniques. In addition the conditions are mild thereby preventing unwanted degradation of the fragile cyclohexapeptides.

Where appropriate, the final cyclohexapeptides may be in the form of pharmaceutically acceptable salts derived from acids such as acetic acid, arachidonic acid, citric acid, glutamic acid, hydrobromic acid, hydrochloric acid, maleic acid, malic acid, oxalic acid, palmitic acid, phosphoric acid, succinic acid, sulfuric acid, tartaric acid and trifluoroacetic acid or bases such as calcium hydroxide, potassium hydroxide and sodium hydroxide. For example, a salt which may be used for caspofungin (1b) is the diacetate and a salt that may be used for micafungin (1c) is the sodium salt.

In a second aspect there is provided a crystalline form of caspofungin diacetate characterized by data selected from the group consisting of:
(a) An XRD powder diffraction pattern with peaks at 2.92±0.2, 5.06±0.2 and 5.88±0.2 degrees 2-theta;
(b) An XRD powder diffraction pattern as depicted in FIG. 1;
(c) Combinations of (a) and (b).

Notably, the crystalline form of caspofungin diacetate of the present invention has a novel morphology resulting from the crystallization approach of the first aspect. When compared to precipitated product as disclosed in WO 2010/008493 it is clear that the present crystalline form of caspofungin diacetate does not reveal a distinct peak in the region 9.0±0.2 degrees 2-theta. The ratio between the intensity of the most intense peak (at 2.92±0.2 degrees 2-theta) and the intensity of any peak in the region 9.0±0.2 degrees 2-theta is at least 10. In the sample depicted in FIG. 1 this is 18.

The water content of the crystalline caspofungin diacetate of the present invention may be from 0.1% to 10% (w/w). Examples of ranges of water content in the cyclohexapeptides of the present invention are from 0.1% to 6% (w/w), from 1% to 8% (w/w), from 2 to 6% (w/w) or from 3.5% to 5.5% (w/w).

The crystalline caspofungin diacetate of the present invention has a purity of at least 99.0% as determined by HPLC. The purity of the sample depicted in FIG. 1 is 99.58%. Impurities are below 0.25% as determined by HPLC. Typically, as found in the sample depicted in FIG. 1, impurities are 0.02%, 0.04%, 0.15% and 0.19%.

LEGEND TO THE FIGURE

FIG. 1 is the XRD spectrum of compound (1b). X-axis: 2-theta value (deg). Y-axis: intensity (cps). Three distinct peaks can be discerned:

| Peak no. | 2-Theta (deg) | Flex width | d-Value | Intensity | I/Io |
|---|---|---|---|---|---|
| 1 | 2.920 | 0.306 | 30.2319 | 20,898 | 100 |
| 2 | 5.060 | 0.329 | 17.4499 | 2,737 | 14 |
| 3 | 5.880 | 0.353 | 15.0181 | 2,751 | 14 |

EXAMPLES

General

X-Ray Powder Diffraction Analysis
Samples were analyzed on an Ultima IV X-ray powder diffractometer from Rigaku.

| Source: | X-ray tube | Target: | Cu |
|---|---|---|---|
| Tube Voltage: | 40 kV | Tube Current: | 40 mA |
| Start Angle: | 2 deg | Stop Angle: | 40 deg |
| Scan Axis: | −2 Theta/Theta | Method: | Continuous |
| Counting Units: | CPS (Counts per sec) | Scan Speed: | 2 deg/min |
| Div slit: | ⅔ deg | DHL slit: | −10 mm |
| Scattering slit: | ⅔ deg | Rec slit: | −0.3 mm |

HPLC Analysis
Injection Volume: 5 μL
Detection: UV (210 and 270 nm)
Flow: 0.35 mL·min$^{-1}$.
Column: Waters XBridge C18, 3.5 μm, 150 mm*2.1 mm (part no 186003023)
Column Temp: 40° C.

Mobile phase A: 50 mM phosphate buffer pH 7 (700 mL)+ acetonitrile (300 mL)"
Mobile phase B: 75% acetonitrile
Gradient:

| Time (min) | 0   | 12 | 15 | 22  | 32  | 34  | 40  |
|------------|-----|----|----|-----|-----|-----|-----|
| % A        | 100 | 84 | 84 | 0   | 0   | 100 | 100 |
| % B        | 0   | 16 | 16 | 100 | 100 | 0   | 0   |

Example 1

Crude Caspofungin Diacetate from Phenylthio Pneumocandin $B_0$ Amine

A solution of phenylthio pneumocandin $B_0$ amine (1.6 L; 17.3 g phenylthio pneumocandin $B_0$ amine; 15 mmol; 44 vol % water) was cooled to −10° C. Under stirring ethylenediamine (EDA; 320 mL; 4.7 mol) was added in 20 minutes between −10 and −3° C. At the start immediately a white precipitate was formed, which dissolved later on. The reaction mixture was stirred for 15 hours at 21-22° C. Additional EDA (170 mL; 2.5 mol) was added at 10-20° C. and stirring at ambient temperature was continued for 31 hours. Under stirring the reaction mixture and acetic acid (1430 mL; 24.7 mol) were simultaneously added to 1.5 L pre-cooled water of 0° C., keeping the temperature below 10° C. and the pH between 5.1 and 5.5 (quenching is exothermic). At 10° C. and pH 5.3 the mixture was extracted with heptane (2×300 mL). To improve the phase separations water (500 mL) was added. The heptane phases were combined and the mix was back-extracted with water (2×250 mL). All aqueous phases were combined and diluted with water to 9.45 L in order to decrease the ethanol content to less than 10%.

Silica gel 100 $C_{18}$ (900 g) was suspended in 75% acetonitrile (2 L). The mixture was placed in a column (height 19.6 cm; internal diameter 10 cm). A bed-volume of 1540 mL was obtained. The column was first washed with 3 bed-volumes 100% acetonitrile and then equilibrated with 3 bed-volumes 0.15% acetic acid in water with a flow of 80 mL·min$^{-1}$ at approximately 1 bar.

The caspofungin solution (9.45 L) as prepared above was used as such for loading on the column. The flow rate was ~50 mL·min$^{-1}$. The flow was adjusted to keep the pressure below 5 bar. The linear flow rate was ~0.6 cm·min$^{-1}$. The loading capacity was 10 g caspofungin diacetate per L resin (12 g total caspofungins per L). Next, the column was washed with 0.15% acetic acid in water (3.2 L) with a flow rate of 70 mL·min$^{-1}$ after which the column was eluted with different solvent compositions at the same flow rate:

10% Acetonitrile/0.15% acetic acid (15 L; 9.7 bed volumes)
13% Acetonitrile/0.15% acetic acid (6375 mL; 4.1 bed volumes)
20% Acetonitrile/0.15% acetic acid (7125 mL; 4.6 bed volumes)

The column was regenerated by washing with 75% acetonitrile/0.15% acetic acid (5625; 3.7 bed volumes). The eluate was monitored continuously with UV (280 nm and 254 nm) and fractions 37-69 were pooled, giving a caspofungin solution of 12.4 L with a yield of 94.7% and a concentration of caspofungin-diacetate of 1.2 g/l 1.2 g·L$^{-1}$ (based on yield and input before column step). The mass balance of caspofungin over all fractions was 99.1%.

Example 2

Hydrophobic Interaction Chromatography and Crystallization of Caspofungin Diacetate A column with a diameter of 10 cm was filled with Amberchrom XT30 resin giving a bed volume of 628 mL and a bed height of 8 cm. The column was equilibrated with 0.15% acetic acid. Loading, washing, and elution were carried out in two subsequent runs. After the first run the column was equilibrated with 0.15% acetic acid. The eluate was monitored continuously with UV (280 nm and 254 nm). The caspofungin solution (12.4 L) as prepared in Example 1 was diluted to 30 L with 0.15% acetic acid (=feed).

Loading 1: Caspofungin feed (21 L) was loaded up-flow on the column (16.7 g caspofungin per L resin) with a flow rate of 80 mL·min$^{-1}$). The linear flow rate was 1.0 cm·min$^{-1}$. The pressure did not exceed 2.5 bar.

Washing 1: The column was washed in down-flow with 0.15% acetic acid (1660 mL).

Elution 1: The column was eluted down-flow with ethanol/0.15% acetic acid (1000 mL). Fractions of 200 mL were collected starting from the point where the UV signal started to rise (after approximately 1 bed volume) and analyzed by HPLC and by Karl-Fischer for water analysis (Table 1).

TABLE 1

Results of column run 1

| Fraction | Dilution | Volume (mL) | Water % (v/v) | Area | Caspofungin Total Area | Yield (%) | Cum. Yield (%) |
|----------|----------|-------------|---------------|------|------------------------|-----------|----------------|
| Feed     | 1        | 21000       | —             | 110.6 | 2323104 | 100  | 100  |
| 1        | 100      | 200         | 22.6          | 84.6  | 1691540 | 72.8 | 72.8 |
| 2        | 100      | 200         | 3.5           | 21.5  | 430940  | 18.6 | 91.4 |
| 3        | 20       | 200         | 0.3           | 9.7   | 38680   | 1.7  | 93.0 |
| 4        | 10       | 200         | n.d.          | 15.2  | 30416   | 1.3  | 94.3 |
| 5        | 10       | 200         | n.d.          | 13.6  | 27248   | 1.2  | 95.5 |

The column was equilibrated with 0.15% acetic acid.

Loading 2: Caspofungin feed (10.345 L) was loaded up-flow on the column (8 g caspofungin per L resin) with a flow rate of 70 mL·min$^{-1}$). The linear flow rate was 0.9 cm·min$^{-1}$. The pressure did not exceed 2.5 bar.

Washing 2: The column was washed up-flow with 0.15% acetic acid (947 mL).

Elution 2: The column was eluted down-flow with ethanol/0.15% acetic acid (735 mL). Fractions were collected starting from the point where the UV signal started to rise (after approximately 1 bed volume) and analyzed by HPLC and by Karl-Fischer for water analysis (Table 2).

TABLE 2

Results of column run 2

| Fraction | Dilution | Volume (mL) | Water % (v/v) | Area | Caspofungin Total Area | Yield (%) | Cum. Yield (%) |
|----------|----------|-------------|---------------|------|------------------------|-----------|----------------|
| Feed     | 1        | 10345       | —             | 77.0  | 796948 | 100  | 100  |
| 1        | 100      | 105         | 26.6          | 54.7  | 574833 | 72.1 | 72.1 |
| 2        | 20       | 100         | 2.7           | 55.9  | 111710 | 14.0 | 86.1 |
| 3        | 5        | 94          | n.d.          | 102.4 | 48136  | 6.0  | 92.2 |
| 4        | 5        | 113         | n.d.          | 58.9  | 33291  | 4.2  | 96.4 |
| 5        | 1        | 113         | n.d.          | 86.3  | 9757   | 1.2  | 97.6 |
| 6        | 1        | 210         | n.d.          | 18.0  | 3782   | 0.5  | 98.1 |

Fractions 1 up to and including 5 of both runs were pooled, giving 1525 mL of a caspofungin solution with an estimated concentration of 9.5 g·L$^{-1}$ (based on yield and input before both runs). The overall yield over both runs was 96.2%. The water concentration of the pooled fractions was analyzed by Karl-Fischer: 5.5%.

The solution obtained above (see Table 3) was used as such for crystallization.

TABLE 3

HPLC results of caspofungin solution after concentration and solvent switch

| Peak no. | Retention time (min) | Peak name | Height (mAU) | Area (mAU*min) | Rel. Area (%) |
|---|---|---|---|---|---|
| 1 | 2.21 | | 1.193 | 0.254 | 0.23 |
| 2 | 9.43 | | 0.003 | 0.020 | 0.02 |
| 3 | 10.23 | | 0.001 | 0.028 | 0.03 |
| 4 | 10.99 | | 0.001 | 0.018 | 0.02 |
| 5 | 12.17 | | 0.579 | 0.160 | 0.14 |
| 6 | 12.68 | Caspofungin | 226.299 | 109.042 | 98.43 |
| 7 | 20.76 | | 3.843 | 0.852 | 0.77 |
| 8 | 21.19 | | 0.007 | 0.327 | 0.29 |
| 9 | 22.73 | | 0.583 | 0.076 | 0.07 |

Thus the caspofungin solution (1.48 L; 9.5 g·L$^{-1}$; 12 mmol) was filtered through a G4 glass-filter after which acetic acid (5 mL; 87 mmol) was added. At ambient temperature ethyl acetate (500 mL) was slowly added in about 30 minutes, causing the temperature to decrease to 16° C. Another portion of ethyl acetate (500 mL) was added in about one hour and again ethyl acetate (100 mL) was added drop-wise and stirring was continued for 30 minutes. The mixture became slightly more turbid. Again ethyl acetate (100 mL) was added drop-wise and stirring was continued for 45 minutes. Finally another portion of ethyl acetate (50 mL) was added and the mixture was stirred at 20° C. for 45 minutes. The ratio ethyl acetate/ethanol (94.5%) was 1.2/1 (v/v). The mixture was turbid and clearly crystals were formed. To increase yield 30 mL ethyl acetate was first added with a constant flow of 0.69 mL·min$^{-1}$ in 45 minutes and then 1220 mL ethyl acetate was added with a constant flow of 1.67 mL·min$^{-1}$ in about 12 hours. The final ratio ethyl acetate/ethanol (94.5%) was 5/3 (v/v). The crystals were filtered off and washed three times with in total 250 mL of a mixture of ethyl acetate/ethanol/water (250/142/8, v/v/v). The wet crystals (15.1 g) were dried under vacuum at 20° C. for 9 hours giving 12.3 g crystals. After this period a smell of ethanol was clearly detected. Therefore a stream of nitrogen was passed through the crystal cake for 1 hour, leading to a weight loss of 0.6 g. Hereafter the crystals were additionally dried for 11 hours, yielding 11.7 g of caspofungin-diacetate as a white crystalline powder (see Table 4) with a water content of 4.9%.

TABLE 4

HPLC results of crystalline caspofungin diacetate

| Peak no. | Retention time (min) | Peak name | Height (mAU) | Area (mAU*min) | Rel. Area (%) |
|---|---|---|---|---|---|
| 1 | 9.43 | | 0.083 | 0.033 | 0.02 |
| 2 | 10.23 | | 0.206 | 0.075 | 0.04 |
| 3 | 10.99 | | 0.003 | 0.033 | 0.02 |
| 4 | 12.17 | | 1.034 | 0.273 | 0.15 |
| 5 | 12.68 | Caspofungin | 408.047 | 179.855 | 99.58 |
| 6 | 20.76 | | 1.704 | 0.339 | 0.19 |

By means of NMR the contents of caspofungin, ethanol, ethyl acetate and acetic acid were determined in the crystals obtained above as follows. Approximately 15 mg of sample and standard (DMB) were accurately weighed in a suitable vial. The samples were dissolved in MeOD by vortexing. The samples were measured at 600 MHz using a delay of 30 s at 300K. The spectra that were used for the calculation of the impurities in the aromatic region were measured using a delay of 5 s and 256 scans to enhance the signal to noise ratio. The analysis was carried out in duplo. Caspofungin was quantified using the tyrosine signal at 7.15 ppm. See Table 5 for results.

TABLE 5

NMR results of crystalline caspofungin diacetate

| | % |
|---|---|
| Caspofungin diacetate | 91.1 (free base: 82.1) |
| Ethanol | 0.2 |
| Acetic acid | 8.8 (2:1 Acetic acid:caspofungin) |
| Ethyl acetate | <0.2 |

The invention claimed is:

1. A method for isolating crystalline caspofungin diacetate comprising the steps of:
   (a) contacting a solution comprising caspofungin and water with a resin;
   (b) removing the liquid phase from the mixture obtained in step (a);
   (c) eluting the caspofungin by contacting material retained after removal of the liquid phase in step (b) by addition of an organic solvent to obtain a mixture thereof;
   (d) separating resin from the mixture obtained in step (c);
   (e) crystallizing the caspofungin from the solution retained after removal of the resin to obtain crystalline caspofungin diacetate in a mixture with the solution; and
   (f) isolating the crystalline caspofungin diacetate from the mixture obtained in step (e), wherein
   the crystalline caspofungin diacetate obtained according to step (e) is characterized by data selected from the group consisting of:
   (i) an XRD powder diffraction pattern with peaks at 2.92±0.2, 5.06±0.2 and 5.88±0.2 degrees 2-theta,
   (ii) an XRD powder diffraction pattern as depicted in FIG. 1, or
   (iii) combinations of (i) and (ii), wherein
   a ratio between an intensity of the peak at 2.92±0.2 degrees 2-theta and an intensity of any peak in the region 9.0±0.2 degrees 2-theta is at least 10.

2. The method according to claim 1, wherein the resin is contained in a chromatography column, and wherein step (a) is carried out by introducing the solution comprising the caspofungin and water onto the chromatography column, and wherein step (b) is carried out by removing the liquid phase from the chromatography column.

3. The method according to claim 1, wherein the resin is washed with an aqueous mixture after step (a) and before step (c).

4. The method according to claim 1, wherein the resin is at least one of a hydrophobic interaction chromatography material, a reversed phase chromatography material, an ion-exchange chromatography material or a mixture thereof.

5. The method according to claim 1, wherein the organic solvent in step (c) is an alcohol.

6. The method according to claim 1, wherein the concentration of the caspofungin in the solution of step (a) is from 2 to 50 times lower than the concentration of the caspofungin in the solution retained after removal of the resin in step (d).

7. The method according to claim 6, wherein the concentration of the caspofungin in the solution of step (a) is from 0.1 to 5 g·l$^{-1}$ and wherein the concentration of the caspofungin in the solution retained after removal of the resin in step (d) is from 5 to 40 g·l$^{-1}$.

8. The method according to claim 6, wherein the amount of water in the solution of step (a) is from 75% to 95%, and wherein the amount of water in the solution retained after removal of the resin in step (d) is less than 10%.

9. The method according to claim 1, wherein the solution of step (a) comprises a water-miscible solvent.

10. Crystalline caspofungin diacetate, characterized by data selected from the group consisting of:
   (a) an XRD powder diffraction pattern with peaks at 2.92±0.2, 5.06±0.2 and 5.88±0.2 degrees 2-theta;
   (b) an XRD powder diffraction pattern as depicted in FIG. 1; or
   (c) combinations of (a) and (b), wherein
   a ratio between an intensity of the peak at 2.92±0.2 degrees 2-theta and an intensity of any peak in the region 9.0±0.2 degrees 2-theta is at least 10.

11. The crystalline caspofungin diacetate according to claim 10, comprising an amount of water from 0.1% to 6% (w/w).

* * * * *